US00PP34594P3

(12) United States Plant Patent
Olesen

(10) Patent No.: US PP34,594 P3
(45) Date of Patent: Sep. 20, 2022

(54) HYBRID TEA ROSE PLANT NAMED 'POULREN033'

(50) Latin Name: *Rosa hybrida*
Varietal Denomination: Poulren033

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 17/300,619

(22) Filed: Sep. 7, 2021

(65) Prior Publication Data

US 2022/0095510 P1 Mar. 24, 2022

(30) Foreign Application Priority Data

Sep. 21, 2020 (QZ) ..... PBR 2020/2247

(51) Int. Cl.
*A01H 5/02* (2018.01)
*A01H 6/74* (2018.01)

(52) U.S. Cl.
USPC ..... Plt./140
CPC ..... *A01H 6/749* (2018.05)

(58) Field of Classification Search
USPC ..... Plt./132, 138, 139, 140
CPC ..... A01H 5/0222
See application file for complete search history.

(56) References Cited

PUBLICATIONS https://www.poulsenroser.dk/en/roses/ShowProduct/68390; Oct. 8, 2021; 2 pages.*

* cited by examiner

*Primary Examiner* — Kent L Bell

(57) ABSTRACT

A new garden rose plant of the Hybrid Tea class which has abundant, red flowers and attractive foliage. This new and distinct variety has shown to be uniform and stable in the resulting generations from asexual propagation.

2 Drawing Sheets

Botanical designation: *Rosa hybrida.*
Variety denomination: 'Poulren033'.

This application claims priority to Plant Breeder's Rights Application Number 2020/2247, which was filed at the Community Plant Variety Rights Office in the European Union on Sep. 21, 2020, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2013 and the resulting seeds were planted in a controlled environment in Fredensborg, Denmark. The new variety, named 'Poulren033', originated as a single seedling from the stated cross.

The new variety may be distinguished from its male pollen parent and female seed parent primarily by the following characteristics. The male pollen parent plant has orange yellow blended flowers while the new variety has red flowers. The female seed parent plant has flowers with a diameter of 80 mm while the new variety has a flower diameter of about 100 mm.

The objective of the hybridization of this rose variety was to create a new and distinct variety with unique qualities, such as:

1. Uniform and abundant red flowers;
2. Vigorous, but compact growth when propagated on its own roots;
3. Exceptional disease resistance.

This combination of qualities is not present in previously available commercial cultivars of this type, known to the inventor, and distinguish 'Poulren033' from all other varieties of which we are aware.

As part of the rose development program, Mogens N. Olesen germinated the seeds from the aforementioned hybridization during winter of 2013 and conducted evaluations on the resulting seedlings in a controlled environment in Fredensborg, Denmark. 'Poulren033' was selected in the spring of 2014 by the inventor as a single plant from the progeny of the aforementioned hybridization.

Asexual reproduction of 'Poulren033' by rooted cuttings was first done by Mogens N. Olesen in the nursery in Fredensborg, Denmark in July, 2014. This initial and other subsequent asexual propagations conducted in controlled environments have demonstrated that the characteristics of 'Poulren033' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulren033'.

Specifically illustrated in FIG. 1 of the drawings are a fully open flower viewed from above, partially opened flower viewed from the side, flower petals detached, sepals detached revealing receptacle and reproductive flower parts.

Figure 1:
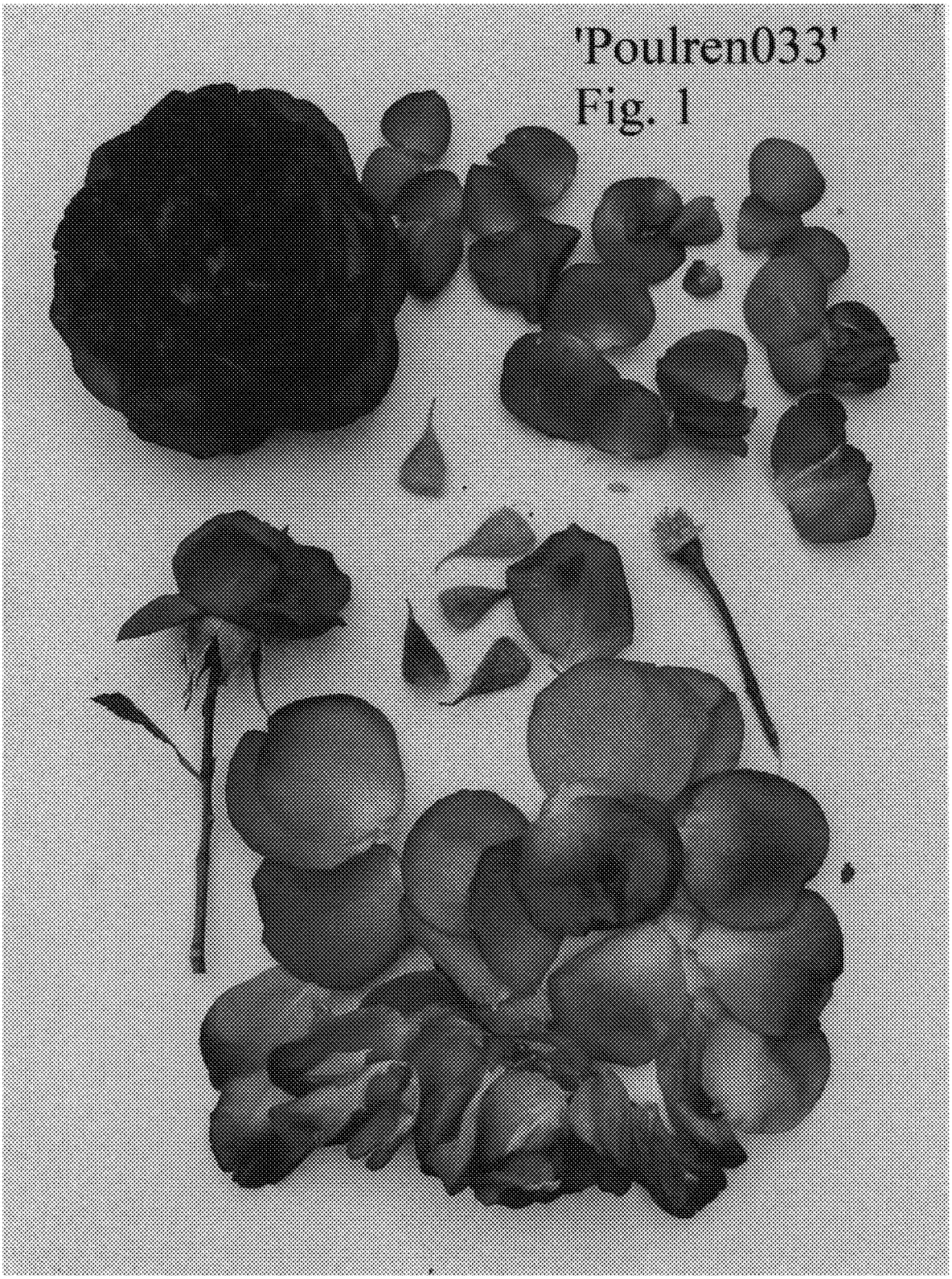
Figure 2:
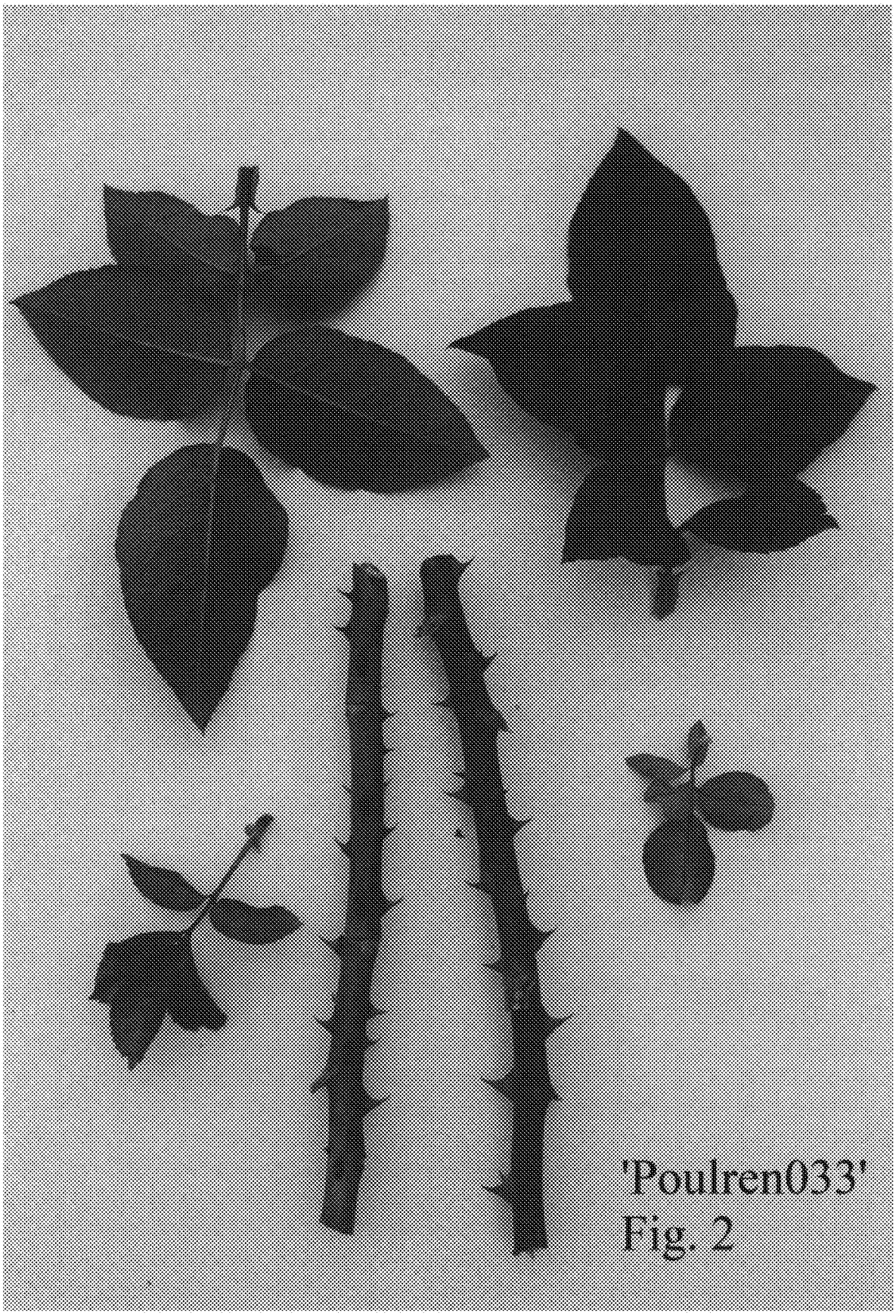

Specifically illustrated in FIG. 2 of the drawings are mature and juvenile leaves, and bare stems exhibiting prickles and anthocyanin.

Plants shown are 2 years of age.

DETAILED DESCRIPTION OF THE VARIETY

The following is a description of 'Poulren033', as observed in its growth in a field nursery in Linn County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulren024', U.S. Plant Pat. No. 26,792 are compared to 'Poulren033' in Chart 1.

CHART 1

| | 'Poulren033' | 'Poulren024' |
|---|---|---|
| Petal Count | 50 | 40 |
| Flower Diameter | 100 mm | 75 mm |
| General Tonality of Flower Color | Red Group 46B | Red Group 46A |

Flower and flower bud:

*Blooming habit*.—Continuous.

*Flower bud*.—Size: Upon opening, 38 mm in length from base of receptacle to end of bud. Bud diameter is 16 mm. Bud form: Ovoid. Sepal inner surface: Color: Yellow-Green Group 146D. Surface: Lightly pubescent. Sepal outer surface: Color: Yellow-Green Group 144A with intonations of Greyed-Purple Group 184B. Texture: Smooth. Sepal Shape: Generally subulate. Apex: Cirrhose. Base: Flat at union with receptacle. Sepal Margin: Margins have weak foliaceous appendages on three of the five sepals. Sepal size: 29 mm long, 11 mm wide. Receptacle: Texture: Smooth. Size: 5 mm in height, 10 mm wide. Color: Yellow-Green Group 144A with intonations of Greyed-Red Group 184C. Shape: Campanulate. Pedicel: Surface: Smooth. Length: 52 mm. Diameter: 3 mm on average. Color: Greyed-Red Group 180A. Strength: Strong.

*Flower bud development*.—Flower buds are borne singly or in clusters of up to 7 fower buds per stem.

*Flower bloom*.—Fragrance: Strong Perfume. Duration: The blooms have a duration on the plant of approximately 14 days. Petals fall cleanly away from plant after flowers have fully matured. Size: Flower diameter is 100 mm when open. Flower depth is 47 mm. Flower shape: Quartered-rosette, very double. Shape of flower, side view: The upper portion is flat. The lower portion is flat convex.

*Petalage*.—Under normal conditions, flowers have about 50 petals.

*General tonality of flower*.—Open flowers are Red Group 46B.

*Petal color of open flower*.—Upper surface: The basal point of attachment has a spot of Yellow Group 4C. At the middle zone petals are Red-Purple Group N57B. At marginal zone Red Group 46B. Occasionally petals are streaked with Red-Purple Group 69D. Lower surface: At the basal point of attachment Yellow Group 4C. At the middle zone Orange Group 27B blending with Red-Purple Group N57B. At marginal zone Red-Purple Group 58A.

*Petals*.—Petal Reflex: Somewhat reflexed. Margin: Entire and uniform. Moderate undulations. Shape: Broad and elliptic. Apex shape: Rounded. Base shape: Acute. Size: 50 mm (l)×50 mm (w). Texture: Smooth. Thickness: Above average.

*Petaloids*.—Size: 15 mm (l) by 12 mm (w). Quantity: About 8. Shape: Elliptical with an acute base and acute apex. Color: The upper side is Red-Purple Group N57B with Red-Purple Group 59B at margins. Petaloid basal spot upper and lower side is Yellow Group 2C. The lower surface is Red-Purple Group N57C with streaks of Red Group 36D.

*Reproductive flower parts*.—Pollen: None observed. Anthers: Size: 2 mm in length. Color: Greyed-Orange Group 163B. Quantity: 41 on average. Filaments: Color: Yellow Group 8D. Length: 10 mm. Pistils: Length: 5 mm. Quantity: 30 on average. Stigmas: Color: Green-White Group 157A. Styles: Color: Green-White Group 157A with other intonations of Red Group 48D. Location of stigmas: Level in location relative to the length of the filaments and the height of the anthers. Hips: None Observed.

Plant:

*Plant growth*.—Upright. Plants are 90 to 100 cm in height, and 55 to 60 cm wide.

*Stems*.—Color of juvenile growth: Yellow-Green Group 144A with intonations of Greyed-Purple Group 183C. Color of mature growth: Yellow-Green Group 144A with intonations of Greyed-Purple Group 183C. Length: Canes are about 45 cm from the base of the plant to the flowering portion. Diameter: About 8 mm. Internodes: On mature canes about 65 mm between nodes. Surface Texture: Young wood: Smooth. Older wood: Smooth.

*Long prickles*.—Incidence: 12 prickles per 10 cm of stem. Size: Average length of prickles on mature stems is 9 mm. Shape: Upper portion is linear. Lower portion is deep concave. Color: Juvenile prickles: Greyed-Purple Group 185B. Mature prickles: Greyed-Purple Group 185B.

*Plant foliage*.—Compound leaf: About 125 mm (l)× 105 mm (w). Quantity: 1 or 2 leaves per 10 cm of stem on average. Leaf bearing angle to the stem: 45 degrees. Color of juvenile foliage: Upper side: Yellow-Green Group 144A with marginal intonations of Greyed-Red Group 180A. Lower side: Yellow-Green Group 144B with shades of Greyed-Red Group 180A. Color of mature foliage: Upper side: Yellow-Green Group 147A. Lower side: Yellow-Green Group 146B.

*Plant leaves and leaflets*.—Stipules: Size: 14 mm long, 6 mm wide. Quantity: 2 per compound leaf. Shape: Linear, slightly broad based with outward extending apices. Margins: Finely serrated. Color: Yellow-Green Group 144A. Petiole: Length: 28 mm. Diameter: 2 mm. Upper surface color: Yellow-Green Group 144A. Lower surface color: Yellow-Green Group 144A. Rachis: Length: 65 mm. Diameter: 2 mm. Upper surface color: Yellow-Green Group 144A. Lower surface color: Yellow-Green Group 144A. Leaflet: Quantity: Normally 5 leaflets. Margins: Serrated. Size: Terminal leaflets are about 65 mm long, 45 mm wide. Shape: Generally elliptical. Base: Rounded. Apex: Acute. Texture: Smooth. Thickness: Average. Arrangement: Odd pinnate. Venation: Reticulate. Glossiness: Very glossy.

*Disease resistance*.—Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

*Cold hardiness*.—The variety is tolerant to USDA Cold Hardiness Zone 6.

*Heat tolerance*.—The variety has been found to be suitable for climate conditions found in the American Horticulture Society heat zone 7.

*Pest resistance*.—The variety is susceptible to any insect pest normally associated with the species.

I claim:

1. A new and distinct variety of rose plant of the Hybrid Tea rose class named 'Poulren033', substantially as illustrated and described herein, due to its abundant red perfumed flowers, disease resistance, and extended period of bloom.

* * * * *

'Poulren033'

'Poulren033'